United States Patent [19]
Norén

[11] Patent Number: 5,871,509
[45] Date of Patent: Feb. 16, 1999

[54] METHOD AND APPARATUS TO REMOVE DATA OUTLIERS, PRODUCED BY EXTERNAL DISTURBANCE, IN INTERNALLY MEASURED SIGNALS IN AN IMPLANTABLE CARDIAC STIMULATOR

[75] Inventor: Kjell Norén, Solna, Sweden

[73] Assignee: Pacesetter AB, Järfalla, Sweden

[21] Appl. No.: 53,691

[22] Filed: Apr. 2, 1998

[51] Int. Cl.$^6$ .................................................. A61N 1/362
[52] U.S. Cl. ............................................. 607/9; 128/901
[58] Field of Search .................................. 607/2, 3, 5, 9, 607/11, 32; 128/901, 902

[56] References Cited

U.S. PATENT DOCUMENTS

| | | |
|---|---|---|
| 5,138,567 | 8/1992 | Mehrgardt . |
| 5,144,568 | 9/1992 | Glover . |
| 5,343,870 | 9/1994 | Gallant et al. . |
| 5,433,209 | 7/1995 | Gallant et al. . |
| 5,527,344 | 6/1996 | Arzbaecher et al. . |

FOREIGN PATENT DOCUMENTS 0 713 714   11/1995   European Pat. Off. .

*Primary Examiner*—Scott M. Getzow
*Attorney, Agent, or Firm*—Hill & Simpson

[57] ABSTRACT

In a method and apparatus for removing data outliers in measured signals in an implanted medical apparatus, such as data outliers produced by GSM disturbance picked up by an implanted cardiac stimulator lead and superimposed on the sensed cardiac activity signal, the signal from the implanted lead is subjected to median filtering. The median filtering minimizes, or eliminates, the effect of highly aberrational data points in the incoming signal, without the necessity of actually removing the components in the signal produced by the disturbance from the incoming signal itself. Since no portion of the actual incoming signal is removed by the median filtering, the data integrity of the sensed cardiac signal is preserved. The signal processed by median filtering, possibly subjected to subsequent post filtering, is then supplied to a detector within the implanted stimulator, which performs the desired detection on the filtered signal, with the result of the detection then being used to control operation of the implanted stimulator.

19 Claims, 9 Drawing Sheets

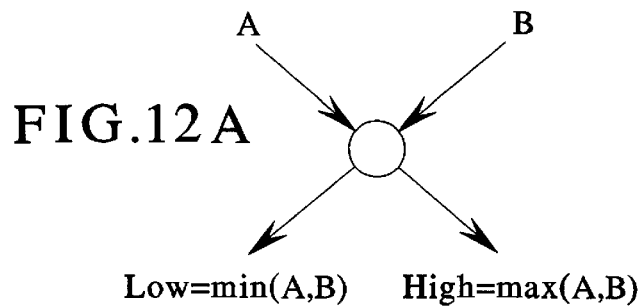
FIG.12A
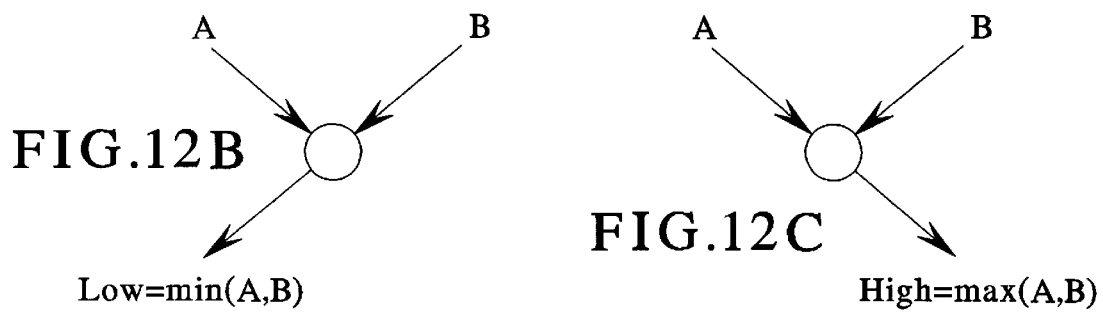
FIG.12B
FIG.12C
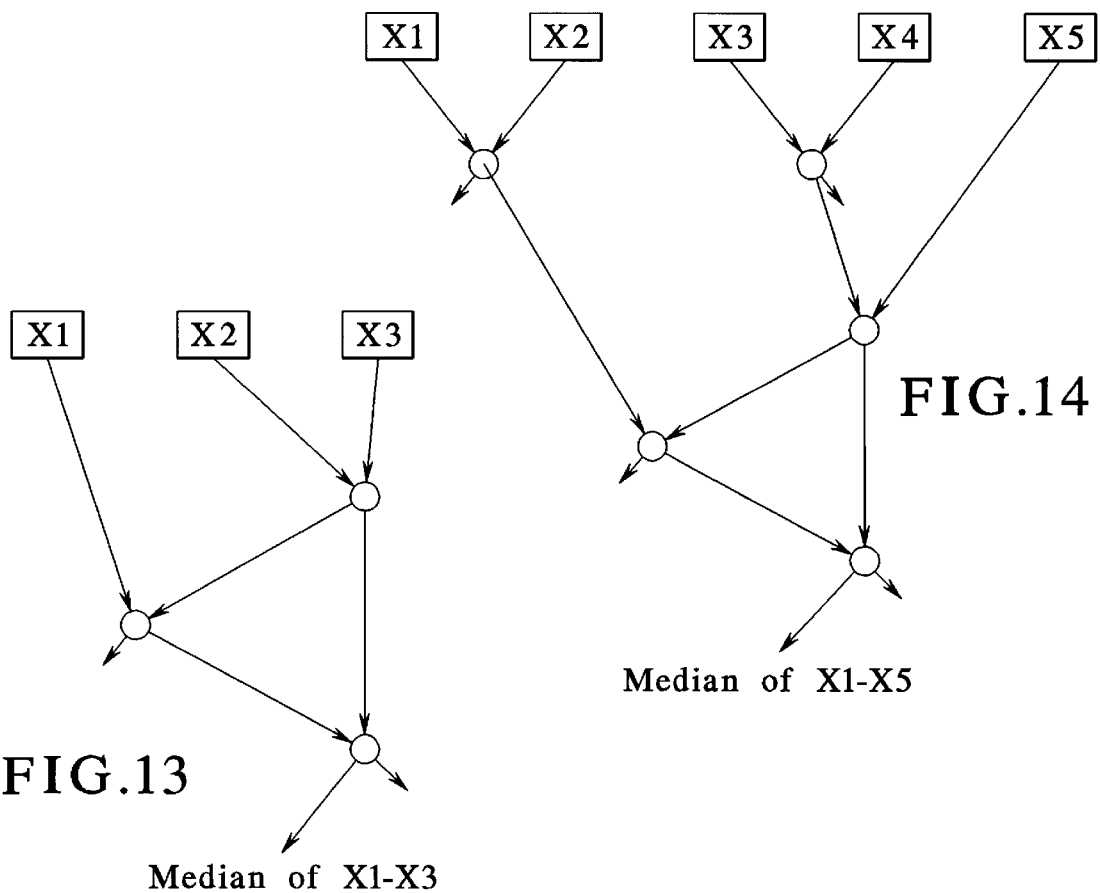
FIG.14
Median of X1-X5
FIG.13
Median of X1-X3

FIG.15A
DATA SELECTOR/MULTIPLEXER
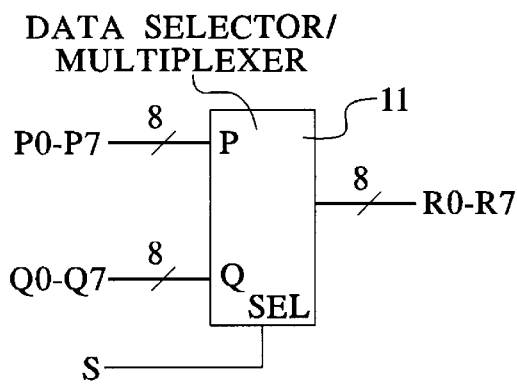
FIG.15B
LOGICAL FUNCTION TABLE
| INPUT SELECT S | MULTIPLEXER OUT R |
|---|---|
| L | P |
| H | Q |
FIG.16A
DATA SELECTOR/MULTIPLEXER
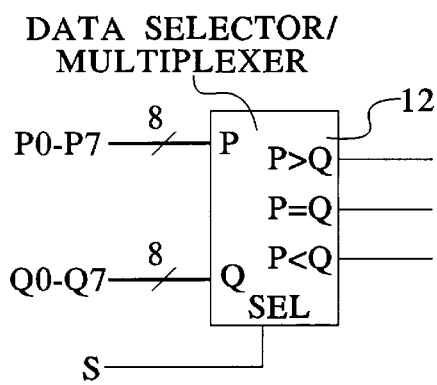
FIG.16B
LOGICAL FUNCTION TABLE
| INPUTS P, Q | COMPARE OUTPUTS | | |
|---|---|---|---|
| | P<Q | P=Q | P>Q |
| P<Q | H | L | L |
| P=Q | L | H | L |
| P>Q | L | L | H |
FIG.18
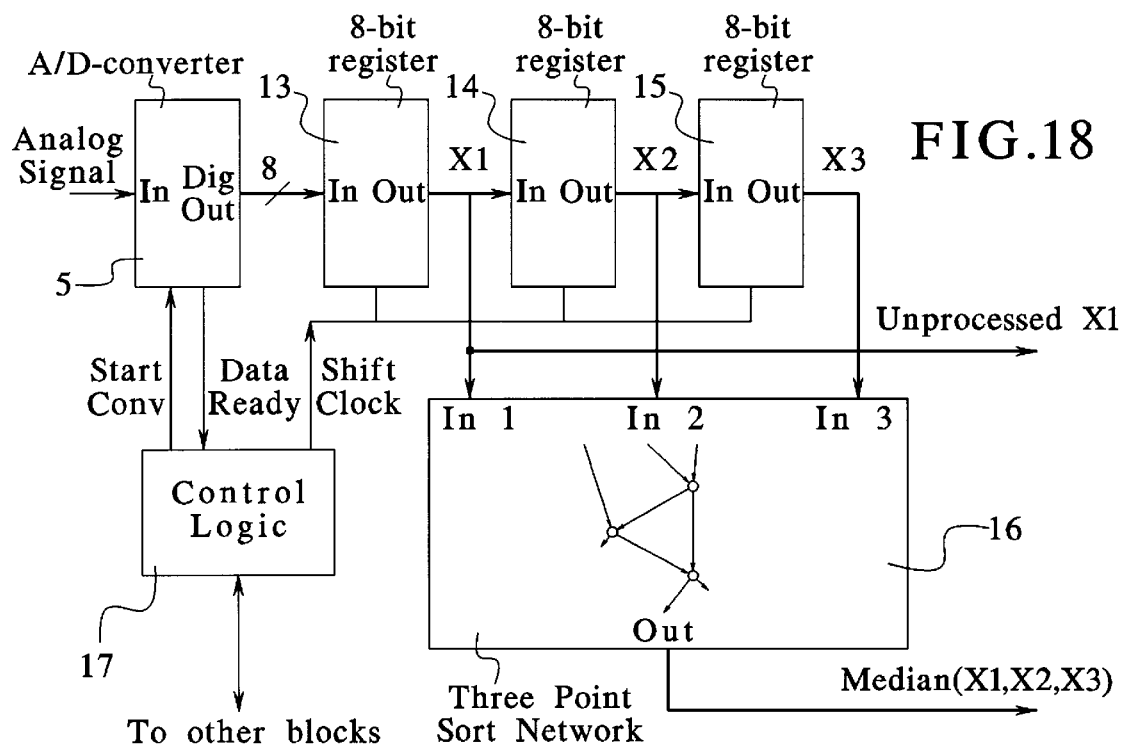

LOGICAL FUNCTION TABLE

| INPUTS A, B | COMPARE OUTPUTS | | | MULTIPLEXER M1 OUT U | MULTIPLEXER M2 OUT V |
|---|---|---|---|---|---|
| | P<Q | P=Q | P>Q | | |
| A<B | H | L | L | A | B |
| A=B | L | H | L | A | A |
| A>B | L | L | H | B | A |

U=min(A,B)   V=max(A,B)

METHOD AND APPARATUS TO REMOVE DATA OUTLIERS, PRODUCED BY EXTERNAL DISTURBANCE, IN INTERNALLY MEASURED SIGNALS IN AN IMPLANTABLE CARDIAC STIMULATOR

BACKGROUND OF THE INVENTION

1. Field of the Invention

The present invention is directed to a method and an apparatus for removing spurious data ("data outliers") produced by externally-originating electromagnetic interference (EMI) from a sensed signal supplied to an implanted medical device, such as a cardiac stimulator.

2. Description of the Prior Art

As is well-known, implanted medical devices, such as cardiac stimulators (pacemakers, defibrillators, etc.) commonly employ an electrode lead, extending from an implanted electronic unit, in order to sense electrical activity in the subject so as to control the electrotherapy (pacing, defibrillation, antitachycardia routine, etc.) administered by the implanted stimulator to the subject. The electrode lead is typically plugged at one end into the implanted electronic unit, and has an opposite end located adjacent cardiac tissue, or in the bloodstream, or at some other appropriate location depending on the type of electrical activity or physiological parameter being sensed. Since this electrode lead contains one or more conductors extending from the implanted device to the sensor or electrode at the tip of the lead, the lead itself acts as an antenna, and thus is susceptible to receiving signals, such as electromagnetic interference (EMI) originating from external sources. Such interference (noise) corrupts the "true" waveform originating from the sensed electrical activity, and therefore when the corrupted sensed signal is analyzed within the implanted device, in order to produce a control signal for the therapy administration, the analysis may be falsified because the noise may produce spurious data points (data outliers) in the analyzed data.

One such type of external interference which is currently under review to determine its impact on implantable medical devices is that produced by cellular telephones. Cellular telephones transmit voice messages by emitting signals from an antenna using radio waves at frequencies between 824 and 894 MHZ. In the system currently in widespread use in the United States, digital cellular hand-held phones employ a maximum of 0.6 watts of power to transmit messages to a cellular transmitter tower. The power level used by the cellular telephone fluctuates throughout the duration of a call. At a large distance from the tower, the hand-held instrument may use the full 0.6 watts. If the caller is closer to the tower, the hand-held telephone may only require 0.05 watts, for example, to effectively transmit the signal. The number of hand-held telephones being used on a system at any given time also affects the transmission power.

Cellular telephones can transmit either analog or digital voice messages, dependent on the type of hand-held instrument and the type of service available. In analog systems, messages are transmitted by modulating or varying either the amplitude of the signal or the frequency of the signal. In digital systems, messages are transmitted in a series of rapid bursts or pulses. An advantage of digital transmission, which is expected to be increasingly employed, is that it increases channel capacity by allowing several users to transmit messages at the same frequency at the same time.

Two types of digital technology currently in use in the United States are relevant to the issue of implanted stimulator/telephone interaction. These are Code Division Multiple Access (CDMA) and Time Divisional Multiple Access (TDMA). In CDMA, messages are transmitted as various sequences of ones and zeros with a special code attached thereto, so that only the intended receiver is able to decode the message. In TDMA, data are transmitted in bursts by turning the signal on and off fifty times per second, causing the signal to have the appearance of a pulsed signal. This technique is therefore sometimes described as "pulse-modulated" RF radiation.

The current standard for use in Europe is the Global Standard For Mobile Communications (GSM) technology. GSM technology uses TDMA technology, and operates in a frequency range between 890 and 960 MHZ. GSM technology uses a 217 Hz pulse rate. The power generated by a GSM portable telephone ranges from 0.02 watts to 2 watts. Generally, the power generated by an instrument designed for use in Europe is higher than an instrument designed for use in the United States, because of the larger distance which the European instrument must transmit its signal in order to reach a base station. The density of base stations in Europe is lower than in the United States.

Because of the widespread use of cellular telephones, a pacemaker wearer will almost certainly randomly enter into and leave the transmission fields of a number of such cellular telephones during the course of a day. Of course, if the pacemaker wearer himself or herself uses such a cellular telephone, the potential is greatest for the signal from that telephone interfering with sensed signals used to control the operation of the pacemaker. It is, of course, well-known in pacemaker technology to filter internally obtained, sensed signals in order to remove noise therefrom, such as noise produced by respiration and other internal sources. Conventional noise removal techniques generally employ some type of filtering, the intention being to remove the noise contribution as much as possible from the overall signal, thereby leaving a filtered signal which constitutes a "clean" representation of the sensed activity or the sensed parameter.

In the case of interference produced by a cellular telephone, particularly a cellular telephone employing GSM technology, the pulses of the GSM signal produce relatively pronounced spikes which are (or may be) superimposed on the internally sensed signal. The amplitude of these spikes usually significantly exceeds the expected amplitude of any portion of the sensed signal. Moreover, the spikes are of extremely short duration. Attempting to filter out the effects of such cellular telephone interference by conventional filtering (such as low-pass filtering, bandpass filtering or high-pass filtering) would unavoidably also remove a large amount of the sensed signal itself, thereby removing an unacceptably high amount of data. Since the data content of the sensed signal is used to control the implanted device, this means that the control of the device will inherently be much less accurate. A device of this type is described, for example, in European Application 0 713 714, which also teaches identification of a noise threshold which, when exceeded, causes one or more remedial measures to be selected.

Median filtering is generally known in the signal processing field as a type of filter which determines a median signal value for a finite neighborhood around each input data point. Examples of median filters described for general signal processing use are found in U.S. Pat. No. 5,114,568 and U.S. Pat. No. 5,138,567. In the field of medical technology, the use of median filtering is generally known for processing ECG signals, as described in U.S. Pat. No. 5,343,870. The use of a median filter for assisting in analyzing an incoming atrial signal to identify the presence of atrial fibrillation is described in U.S. Pat. No. 5,527,344.

SUMMARY OF THE INVENTION

It is an object of the present invention to provide a method and an apparatus for removing spurious data from internally sensed signals, which are used to control an implanted stimulator, and which are subject to externally-originating electromagnetic interference, without simultaneously removing a significant amount of data contained in the sensed signal itself.

It is a further object of the present invention to provide such a method and apparatus wherein the sensed signal is filtered, so as to remove externally-originating noise therefrom, while retaining as much of the data integrity of the original signal as possible.

The above object is achieved in accordance with the principles of the present invention in a method and apparatus wherein the sensed signal, with externally originating electromagnetic interference superimposed thereon, is subjected to median filtering before a control signal is derived therefrom which is used to control the operation of the implanted stimulator. Median filtering does not attempt to "remove" the noise which is superimposed on the original signal, and therefore the use of median filtering does not present the risk that a portion of the sensed or measured data will be removed together with the noise. Instead, median filtering functions by rejecting, or minimizing the effect of, spurious data within the overall signal.

Median filtering is a known non-linear filtering technique which has been in general use in signal processing technology for removing noise spikes, but has not heretofore been used within an implantable medical device for the purpose of removing spike-type externally-originating noise which is superimposed on an internally sensed or measured signal.

In general, a median filter sorts a number of incoming signals as to amplitude, and replaces the current value of a signal by the median value of the sorted signal sequence. The length or depth of a median filter is defined by the number of times that such a median is formed and applied during the sorting. The median which is calculated in each element of a median filter, is the value (amplitude) for which an equal number of values exist above and below. The absolute values of the amplitudes thus are not relevant to the filtering which takes place in a median filter; it is only taken into account whether the amplitudes fall above or below a particular value. For example, the median of the sequence 24, 19, 16, 18, 20 is 19, because two values in the sequence fall below 19 and two values in the sequence are above 19. This would not change even if the first number, for example, were 34 instead of 24. If the numbers in this sequence represented amplitudes of incoming signals, and if the unusually high number 34 represented a signal spike, such as produced by a GSM technology cellular phone signal, the median filter (in this simple example) would maintain the same median, even in the presence of this spike. It is therefore not necessary in the context of median filtering to "remove" the spike itself, but the presence of the spike does not significantly affect the value of the output signal of the median filter.

The use of median filtering therefore represents a different conceptual approach from the type of filtering conventionally employed to remove noise from incoming sensed signals in an implanted stimulator. The noise (i.e. the spike) in median filtering is allowed to remain in the signal, but its effect on the median filtered output signal is negligible, or it may have no effect at all. Since it is not necessary to try to remove the spike, there is no risk of removing valid data along with the noise, and thus the data integrity of the "true" sensed or measured signal is maintained or preserved.

In a preferred embodiment of an implantable cardiac stimulator constructed and operating in accordance with the inventive method and apparatus, an incoming sensed or measured signal with noise superimposed thereon is first subjected to signal editing such as amplification and low-pass filtering, and the edited signal is then supplied to an analog-to-digital converter. The digital output of this converter is then supplied to a median filter. The output of the median filter, if desired, may be subjected to post-filtering, such as bandpass filtering. The final, filtered signal is then supplied to a detector or an analyzer which undertakes any type of appropriate analysis of the signal, dependent on the features which are desired to be extracted therefrom for controlling the implanted stimulator. The output of the detector is then supplied to one or more control stages of the device, and the therapy administered by the device is appropriately controlled thereby.

DESCRIPTION OF THE DRAWINGS

FIGS. 12A, 12B and 12C respectively show symbolic notation for the various types of sorting nodes employed in a network for median filtering in accordance with the invention.

FIG. 13 is a schematic illustration of a network for median filtering from a threepoint input.

FIG. 14 is a schematic illustration of a network for median filtering from a fivepoint input.

FIG. 15A shows a data selector/multiplexer which can be used as a component in a sorting node in a median filter constructed in accordance with the present invention, and FIG. 15B shows the logical function table associated therewith.

FIG. 16A shows a magnitude comparator which can be a component in a sorting node in a median filter in accordance with the invention, and FIG. 16B shows the logical function table associated therewith.

FIG. 18 is a schematic block diagram of a three-point median filter constructed in accordance with the principles of the present invention.

DESCRIPTION OF THE PREFERRED EMBODIMENTS

Figure 1:
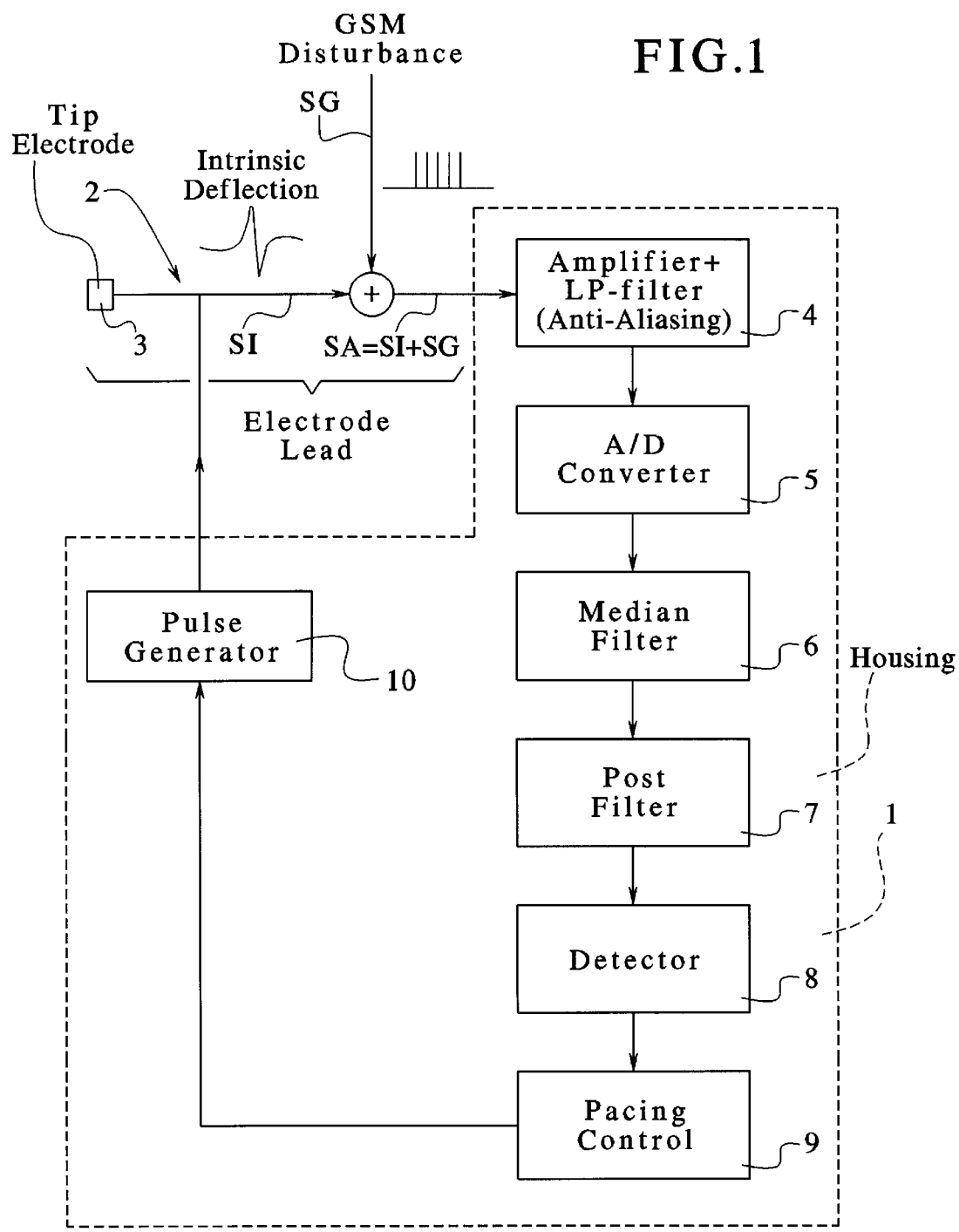
FIG. 1 is a schematic block diagram of a cardiac stimulator, in the example of a pacemaker, constructed and operating in accordance with the principles of the present invention.

FIG. 1 shows a schematic block diagram of the basic components of an implantable cardiac stimulator employing median filtering for removing data outliers from a measured signal in accordance with the invention. The example shown in FIG. 1 is an implantable pacemaker, but the invention is applicable to any type of implantable medical therapy administration device which is subject to externally originating (extracorporeally-produced) noise being superimposed on an internally measured (intracorporeally-produced) signal.

All of the components in the pacemaker shown in FIG. 1 are contained in an implantable housing 1, having an electrode lead 2 connected thereto with a tip 3 which, when implanted, is in contact with cardiac tissue of a patient, for delivering stimulation pulses to the tissue, and for measuring (sensing) cardiac electrical activity. In the example shown in FIG. 1, the lead is a unipolar lead, and therefore pulses are delivered and sensing takes place in a circuit which includes body tissue between the tip electrode 3 of the electrode lead 2 and the housing 1.

The sensed intrinsic deflection signal is supplied to an input amplifier 4, which may also perform low-pass filtering. In general, the amplifier 4 performs an anti-aliasing function. As noted above, the electrode lead 2 in effect constitutes an antenna, which is susceptible to receiving disturbance signals, which will be superimposed on the sensed signal. In the example shown in FIG. 1, the sensed signal is represented as an intrinsic deflection signal Si, and this is superimposed with externally-originating disturbance, in the example of FIG. 1 this disturbance being GSM disturbance SG. (This superimposition of the disturbance SG on the sensed signal Si is represented symbolically by an adder in FIG. 1, however, this is merely for illustrative purposes and a hardware component corresponding to this adder does not exist in the actual pacemaker.) The input signal SA supplied to the input amplifier 4 is therefore the sum SI+SG.

The output of the input amplifier 4 is supplied to an analog-to-digital converter 5, which produces a digital output signal corresponding the input analog signal in a known manner. This digital output signal is supplied from the converter 5 to a median filter 6, the detailed operation of which is described below. In general, the median filter performs the function of removing data outliers which may exist in the digital signal from the converter 5 representing the amplified and low-pass filtered input signal SA.

The output of the median filter 6 is supplied to a post filter 7. The output of the post filter 7 represents the processed signal which is supplied to a detector 8. This post filter 7 may be a smoothing (low-pass) filter, but in the exemplary embodiment shown in FIG. 1 a bandpass filter is used. Such a bandpass filter may have a passband in a range between 10–100 Hz. The post filter 7 may alternatively be a simple moving average filter.

The detector 8 may be of any known type, dependent on the type of information which is desired to be extracted from the processed signal. The output of the detector 8 is supplied to pacing control logic 9, which formulates a pacing control signal in a known manner dependent on the processed signal. The pacing control signal is supplied to a stimulation pulse generator 10, which emits stimulation pulses which are supplied to the patient via the electrode 2. The pacing control signal, for example, can modify the stimulation rate and/or the amplitude of the stimulation pulses emitted by the pulse generator 10.

Figure 2:
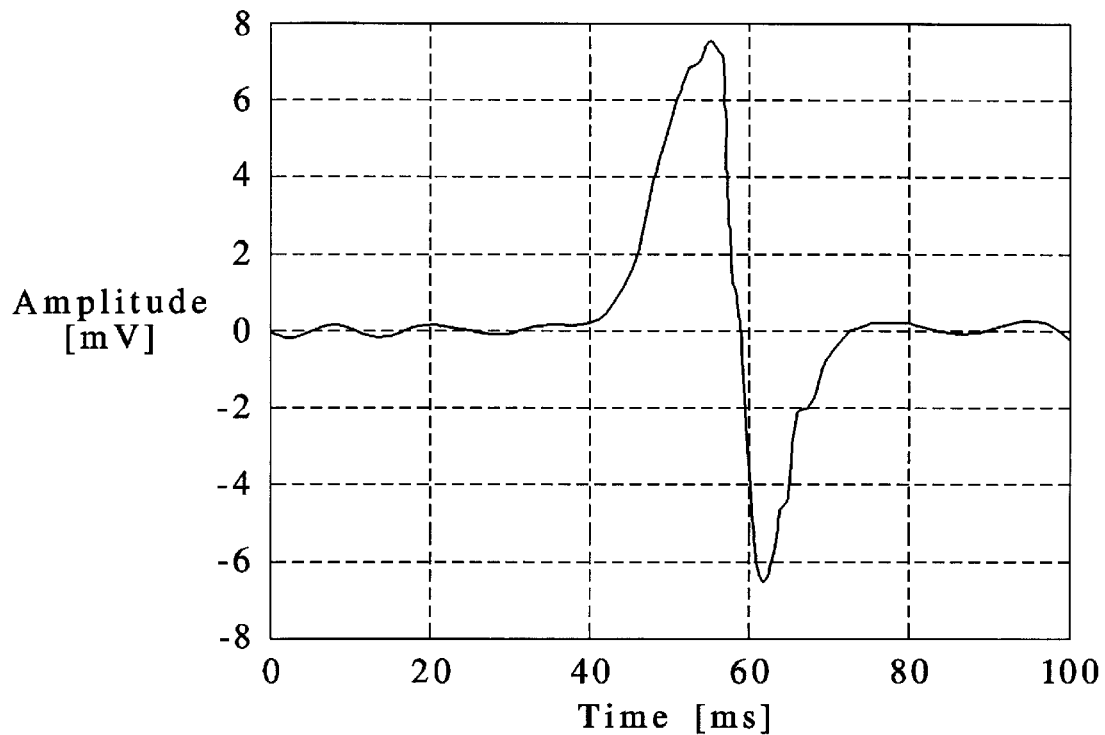
FIG. 2 is a voltage/time diagram of a typical intrinsic deflection signal.

A more detailed and enlarged voltage/time diagram of the intrinsic deflection signal SI obtained by unipolar sensing is shown in FIG. 2. As is well-known to those of ordinary skill in the art, the amplitudes and time durations in this figure, and in other voltage/time diagrams shown herein, will vary depending on electrode placement and the patient. Typical values, as represented in FIG. 2, are that the signal SI has a positive upward slope of a duration between 2–20 ms, and a negative downward slope of a duration of approximately 4–10 ms, and a peak-to-peak voltage of between approximately 4–20 mV. In this example, the signal SI represents a P-wave measured with the electrode tip 3 placed in the atrium. The peak-to-peak amplitude may then in extreme cases be 10 mV. If the electrode is floating the amplitude will be between 0.20–0.3 mV.

Figure 3:
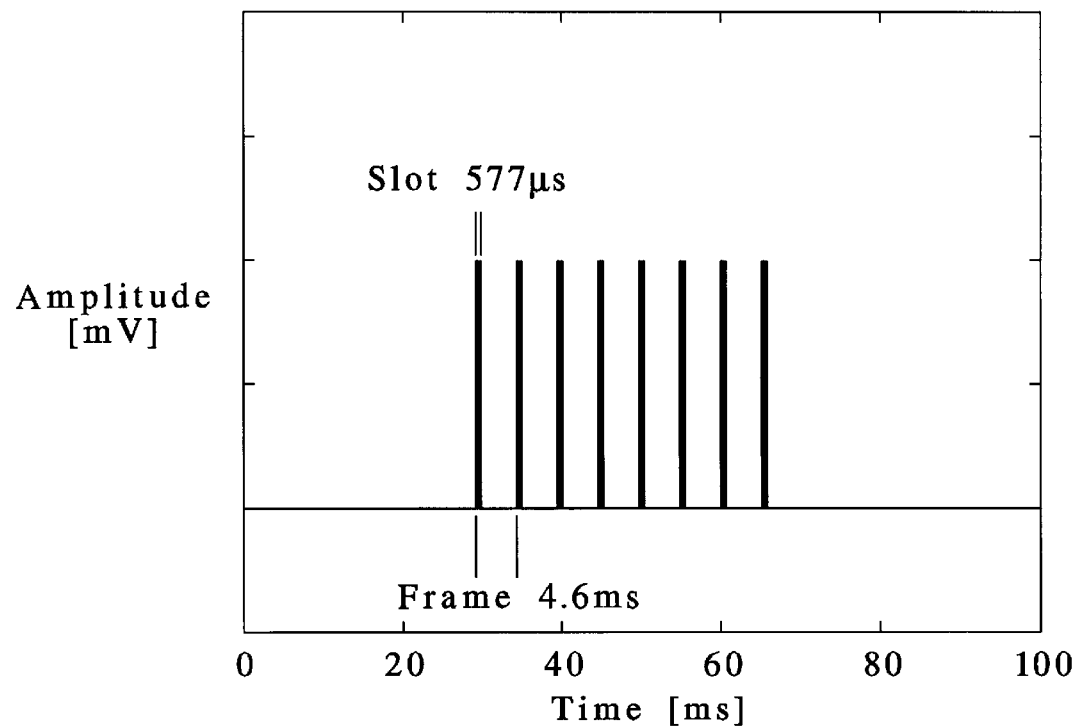
FIG. 3 is a voltage/time diagram of a typical disturbance signal produced by GSM transmission.

FIG. 3 shows an example of a typical GSM transmission signal, comprising the disturbance signal in the example under discussion. The shown in FIG. 3 is an example of a pulse train in a GSM system operating with discontinues transmission (DTX). The first pulse in the series is referred to in GSM transmission terminology as the "idle" pulse, and the following seven pulses comprise the "silence descriptor" (SID).

Figure 4:
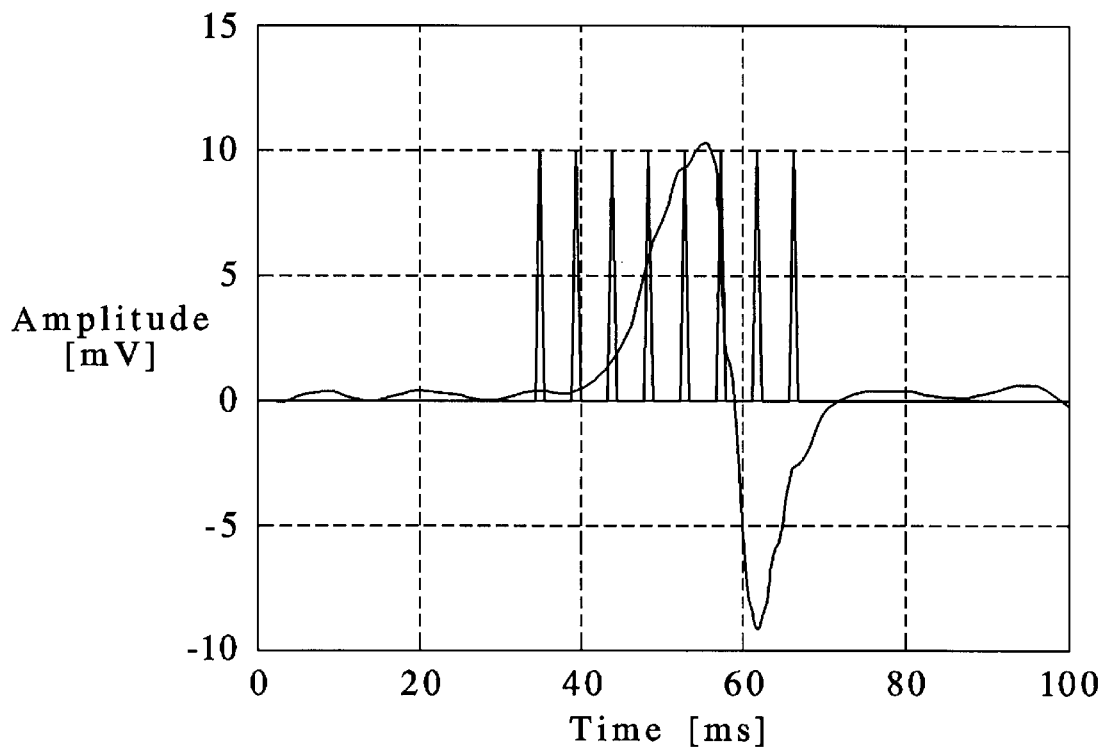
FIG. 4 is a voltage/time diagram of the signal which results from the imposition of the disturbance signal of FIG. 3 on the intrinsic deflection signal of FIG. 2.

FIG. 4 shows the signal which arises as a result of the GSM disturbance on the conductor within the electrode lead 2, in the same graph with the intrinsic deflection signal SI, so that a comparison of amplitudes and durations can be seen. FIG. 4 does not represent the actual superimposition of the disturbance signal SG on sensed signal SI (this being shown below in FIG. 10). It should be noted that in this example, positive GSM disturbance is being used to exemplify the disturbance signal SG. Negative GSM disturbance also occurs, which appears the same as the positive GSM disturbance shown in FIG. 3, but with a negative amplitude. The principles described herein are the same regardless of whether the disturbance signal is characterized as positive or negative.

Figure 5:
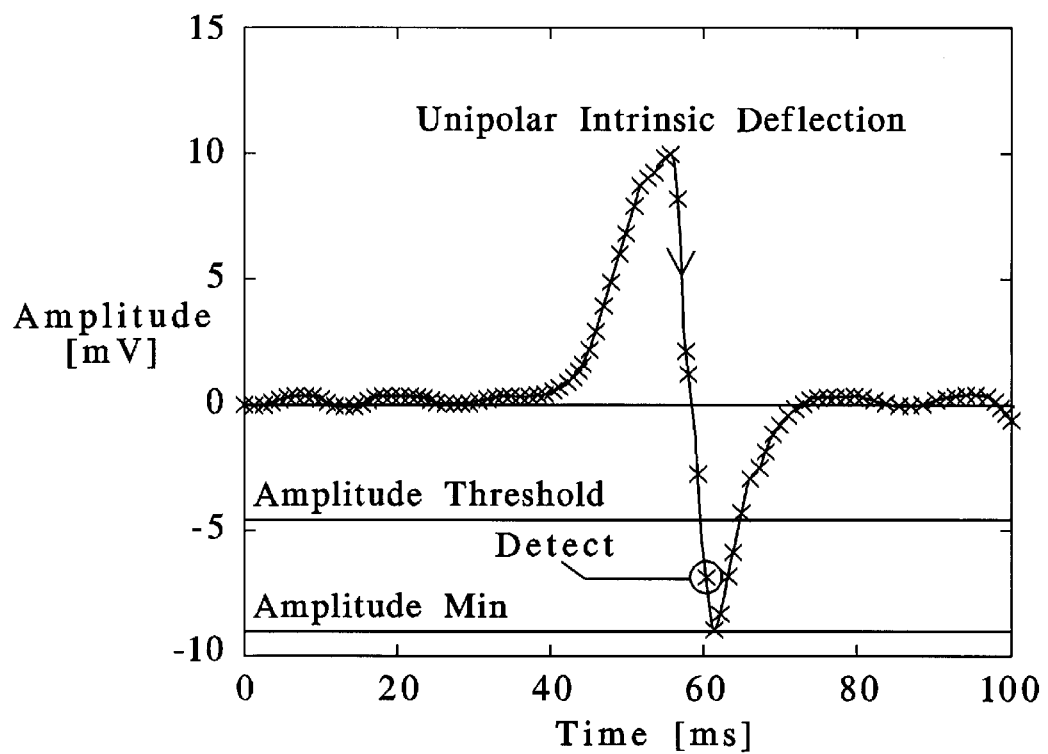
FIG. 5 is a voltage/time diagram illustrating the operation of the detector constructed and operating in accordance with the principles of the present invention.

FIG. 5 is a voltage/time diagram for describing the detecting function performed by the detector 8. Many detection techniques and algorithms are well-known to those of ordinary skill in the art, and other techniques may be employed besides or in addition to the exemplary detection approach described herein. In the detection technique exemplified in FIG. 5, a heart event is considered to be detected when the signal first passes an amplitude threshold, which is typically set to half of the value of a programmed amplitude minimum. Using a sampling frequency of, for example, 1024 Hz, the points in time at which a digital signal (pulse) is produced by the converter 5, based on the amplitude of the analog signal, are each represented by an X in FIG. 5. The first-occurring digital pulse having an amplitude below the amplitude threshold is circled in FIG. 5, and this is taken as the detection point.

Figure 6:
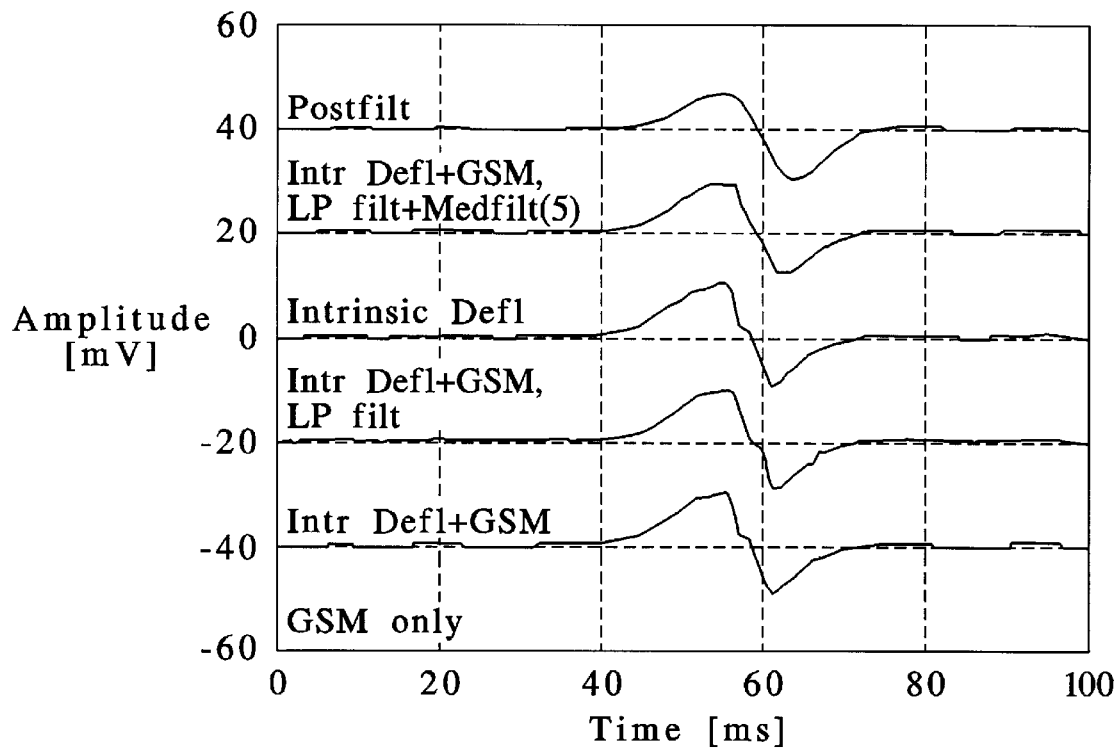
FIG. 6 is a voltage/time diagram showing signals for comparing the detection point of FIG. 5 with and without median filtering for a clean intrinsic deflection signal without external disturbance.

FIG. 6 shows a set of related curves for use in comparing the detection point with and without a median filter 6 plus the post filter 7 for a "clean" intrinsic deflection signal SI, without any external disturbance. The signal Posffilt is the input signal to the detector 8, i.e., the "smooth" output from the post filter 7. The signal designated Intr Defl+GSM, LP Filt+Medfilt(5) is the output signal from the median filter 6 (i.e., just before the post filter 7, the designation (5) indicating that a five-point median filter has been used. The signal Intrinsic Defl is the "clean" unipolar intrinsic deflection signal SI, with no disturbance added thereon. The signal designate Intr Defl+GSM, Lpfilt is the amplified (with gain=1) and low-pass filtered signal supplied at the output of the input amplifier 4. In this case, since there is no disturbance, the GSM contribution to this signal is zero. The signal Intr Defl+GSM is the input signal SA to the input amplifier 4. Again, since an absence of disturbance being assumed for this initial case, the GSM contribution to this signal is zero, i.e., SA=SI.

The signal designated GSM Only represents the disturbance signal (in the discussion below), but in this case since there is no disturbance this signal has a constant zero value.

Figure 7:
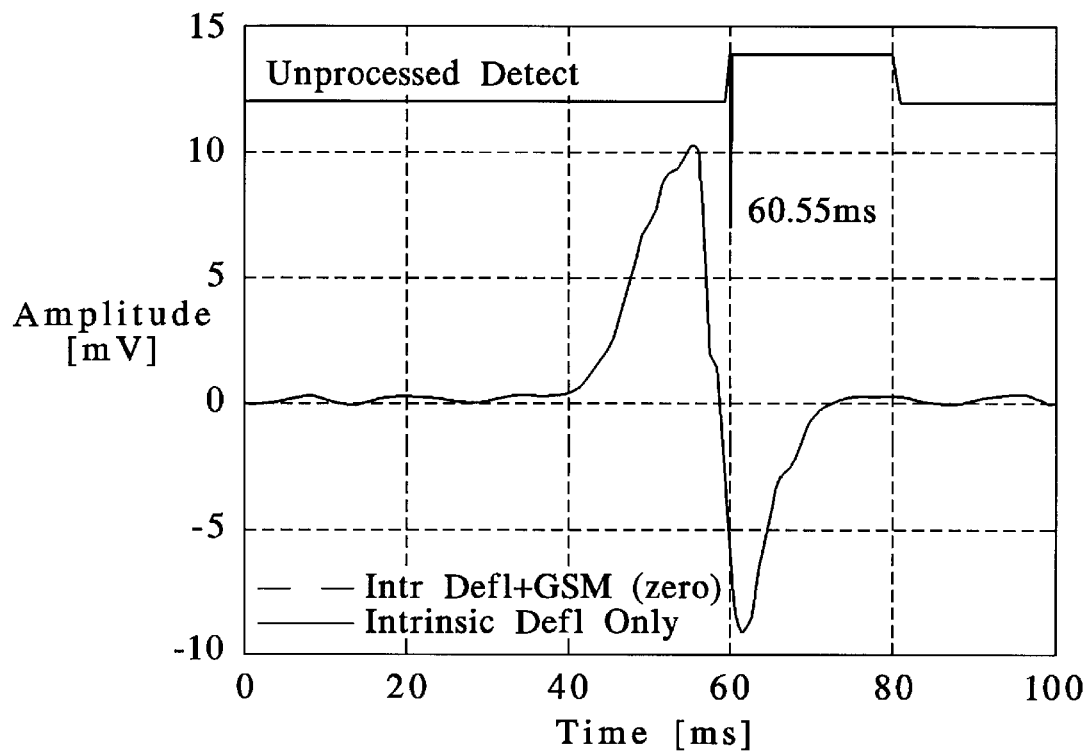
FIG. 7 is a voltage/time diagram showing the intrinsic deflection signal and an unprocessed (no median filtering and no post filtering) signal.

FIG. 7 shows the unprocessed detection signal Unprocessed Detect, for the case shown in FIG. 6. Since the disturbance is zero, the signal lntr Defl+GSM and the signal Intrinsic Defl Only coincide. The term "unprocessed" in the context of FIG. 7 means that no median filtering and no post filtering were undertaken. This case can be considered as if the input of the detector 8 were directly connected to the output of the converter 5. This is for the purpose of identifying an "ideal" detection point for use as a benchmark in subsequent comparisons. As shown in FIG. 7, the ideal detection point in this case is at 60.55 ms.

Figure 8:
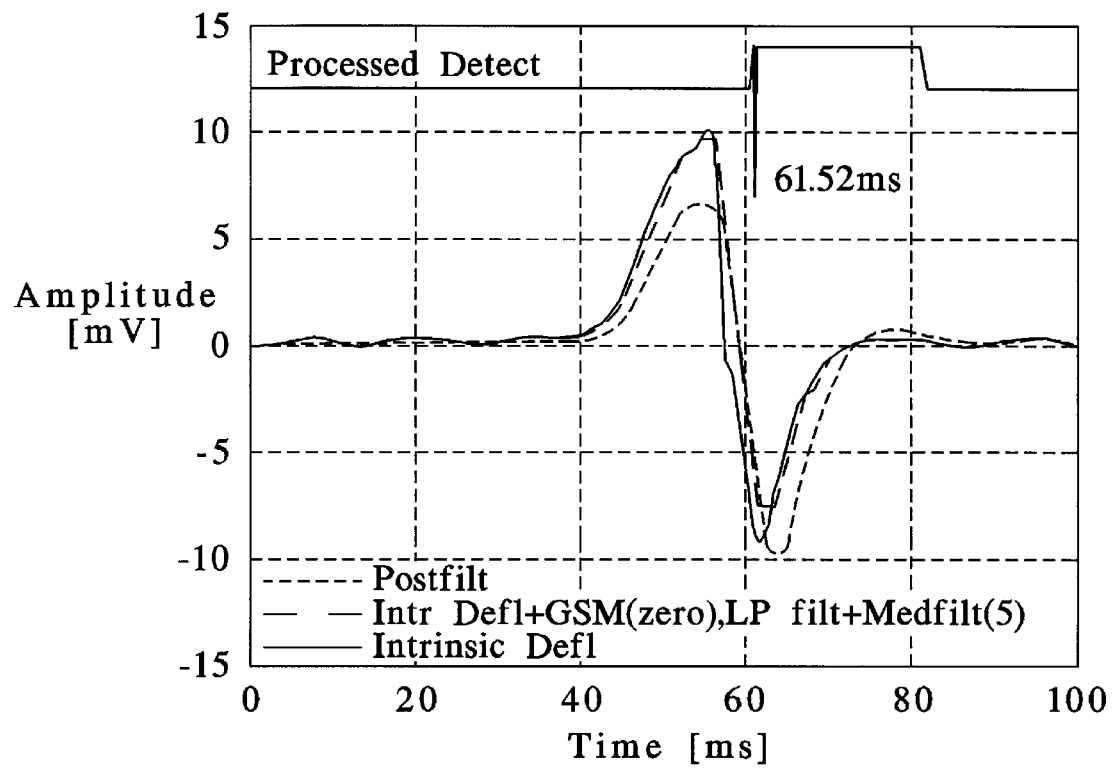
FIG. 8 is a voltage/time diagram showing the intrinsic deflection signal and the processed detection signal with median filtering and post filtering.

FIG. 8 shows the processed detect signal Processed Detect, which represents the detection time when median filtering and post filtering are used, i.e., all components are connected as shown in FIG. 1. Again, the input signal is the "clean" intrinsic deflection signal SI shown in FIG. 6. As a result of the processing which takes place in the median filter 6 and the post filter 7, the detection point is now at 61.52 ms. This represents a short delay of approximately 1 ms from the ideal case represented in FIG. 7. As noted above, the designation (5) indicates that a five-point median filter was used.

Figure 9:
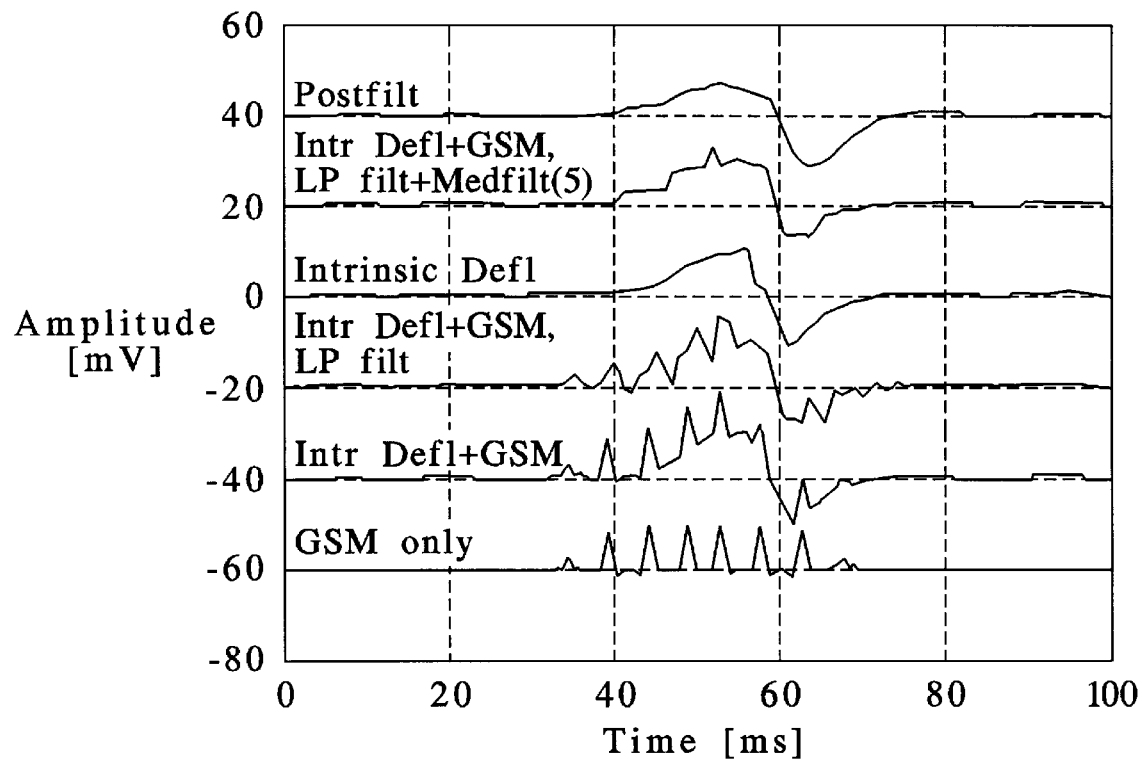
FIG. 9 is a voltage/time diagram showing signals arising in the case of an intrinsic deflection signal with GSM disturbance.
Figure 10:
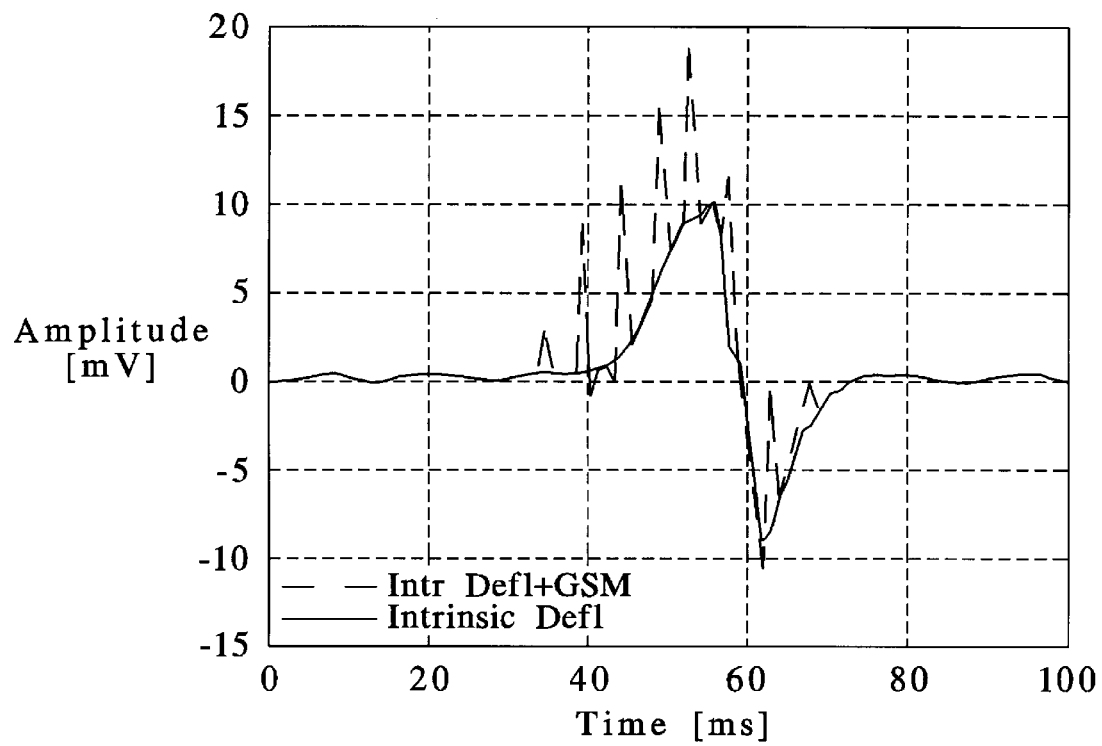
FIG. 10 is a voltage/time diagram showing an undisturbed intrinsic deflection signal, and an intrinsic deflection signal disturbed by GSM disturbance.
Figure 11:
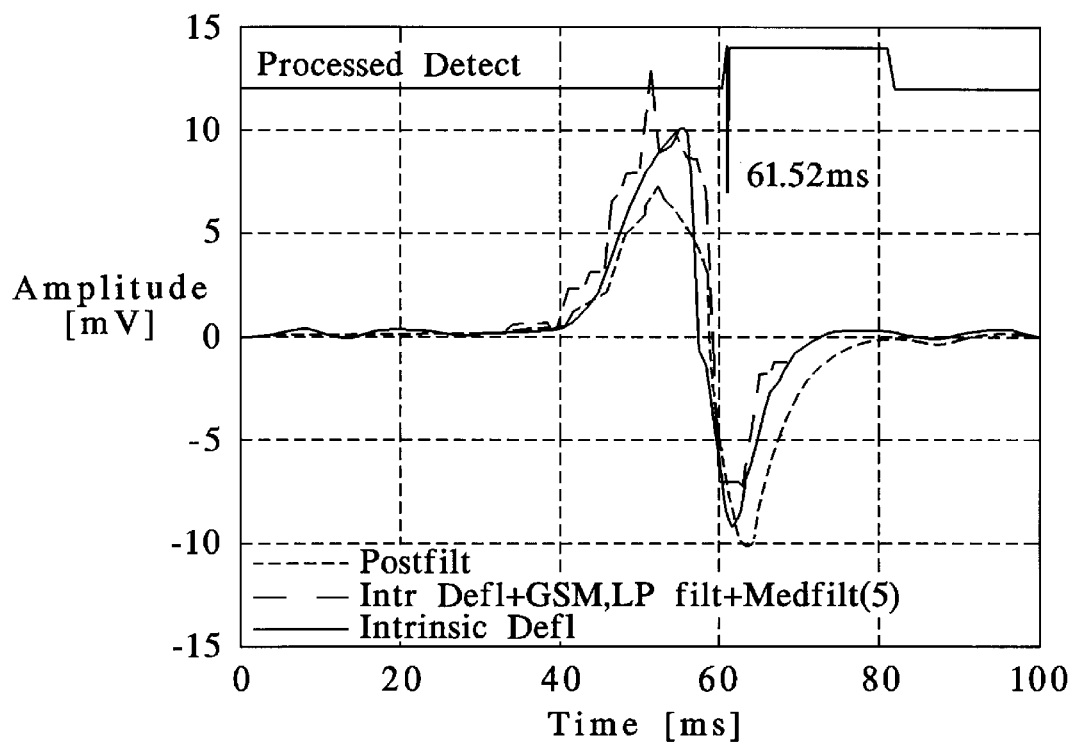
FIG. 11 is a voltage/time diagram for comparison of the detection point for an undisturbed signal and the signal of FIG. 10, processed (filtered) in accordance with the invention.

FIG. 9 shows the same set of curves as was described in connection with FIG. 6, this time in the presence of a GSM disturbance SG, which produces the signal designated GSM Only shown in FIG. 9. This disturbance is shown superimposed on the intrinsic deflection signal in the signal designated Intr Defl+GSM in FIG. 9. A "zoom" of this signal is shown in FIG. 10. The effect of median filtering and post filtering in accordance with the invention on the cardiac event detection is shown in FIG. 11, wherein it can be seen that the detection point is unchanged compared to the detection point associated with the undisturbed signal.

As noted above, median filtering, in general, is a technique which has previously been employed in signal processing, although not for the specific purpose nor to achieve the specific results described herein. The following discussion presents known examples of median filter hardware which can be used to accomplish the median filtering employed herein.

As noted above, a median filter is basically a sorting network, with sorting successively taking place at a number of nodes. Symbolic notations for the three basic types of nodes employed in a median filter are respectively shown in FIGS. 12A, 12B and 12C. Each node has two inputs, respectively designated in the symbolic notation as A and B. The node shown in FIG. 12A produces two outputs, one of which is designated as the low output, and constitutes the minimum of A and B. The other output is the high output, which constitutes the maximum of A and B. The node symbolically represented in FIG. 12B produces only a low output, and the node symbolically represented in FIG. 12C produces only a high output.

FIG. 13 shows the basic structure, using the symbolism from FIGS. 12A, 12B and 12C, for a network (median filter) which produces a median from a three-point input, the inputs respectively being X1, X2 and X3. The resulting output is the median of the three input values. FIG. 14 shows the basic structure of a network (median filter) for producing the median from a five-point input, the inputs being X1, X2, X3, X4 and X5. Higher order filters (networks) can be devised along the same principle.

FIG. 1 5A shows a block diagram of a data selector/multiplexer 11 which can be used in an exemplary embodiment of a hardware realization of a sorting node in the median filter 6 employed in the invention. FIG. 16A shows a block diagram of a data magnitude comparator 12 usable in combination with the data selector/multiplexer 11 shown in FIG. 15A to build a sorting node. The depiction of these components as having parallel 8-bit input buses assumes that the resolution of the analog-to-digital converter 5 is 8-bits, and that the output of the converter 5 is supplied on a 8-bit bus as well. FIG. 15B shows the logical function table for the data selector/multiplexer 11 of FIG. 15A, and FIG. 16B shows the logical function table for the magnitude comparator 12 of FIG. 16A.

Figures 17A, 17B:
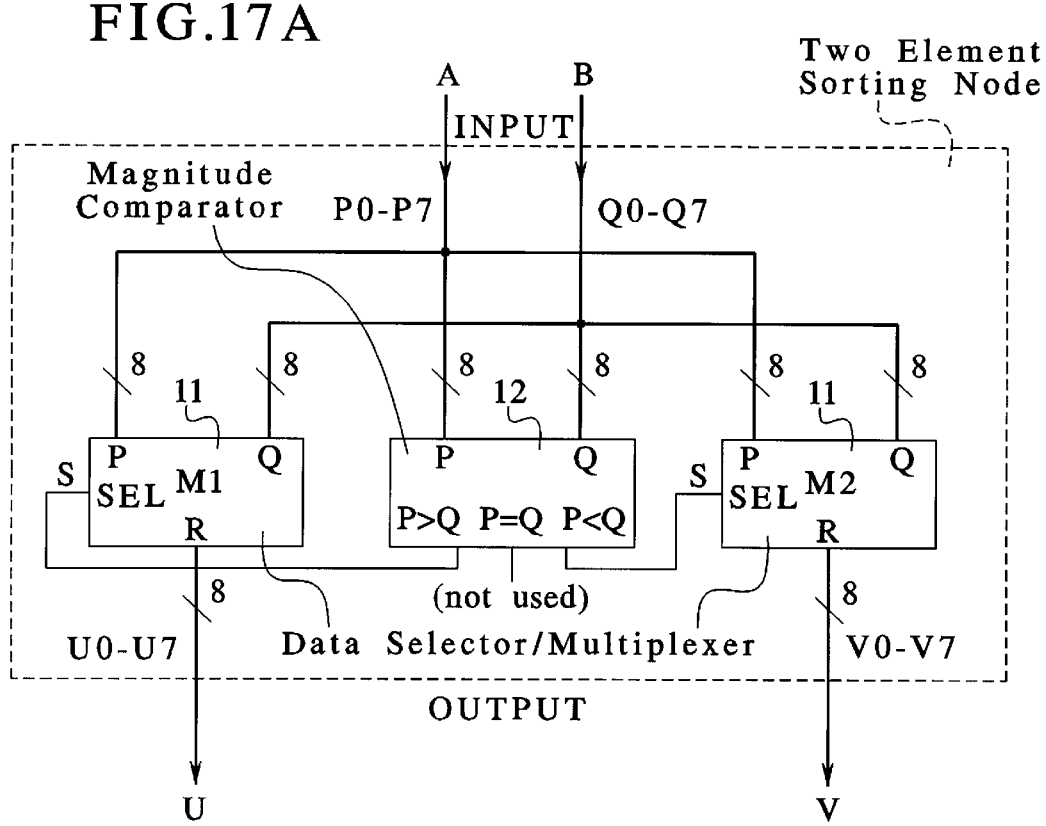
FIG. 17A is a block diagram of a two element sorting node employed in a network for median filtering in accordance with the invention.
FIG. 17B shows the logical function table associated therewith.

An exemplary combination of these components to form a two element sorting node is shown in FIG. 17A, with the logical function table therefor being shown in FIG. 17B. The hardware embodiment shown in FIG. 17A is for a sorting node as symbolically represented in FIG. 12A, having both a low output (designated U in FIG. 17A) and a high output (designated V in FIG. 17A). For constructing a sorting node as symbolically represented in FIG. 12B, having a minimum output only, the multiplexer M2 is omitted from the circuitry shown in FIG. 17A. For constructing a sorting node as symbolically represented in FIG. 12C, having maximum output only, the multiplexer M1 is omitted from the circuitry of FIG. 17A.

FIG. 18 is a block diagram of a hardware realization of a three-point median filter as an exemplary embodiment of the median filter 6 of FIG. 1. In the exemplary embodiment shown in FIG. 18, the respective inputs X1, X2 and X3 are produced by shift registers 13, 14 and 15. These inputs are supplied to a three-point sorting network 16 as described in connection with FIG. 13. Each sorting node of the three-point sorting network 16 may be constructed as shown in FIG. 17A. The analog-to-digital converter 5 and the shift registers 13, 14 and 15 are shown in FIG. 18 as being operated by clock signals from control logic 17. The control logic 17 need not be a separate component, but can be embodied in the overall pacing control logic 9, in the form of a suitably programmed microprocessor.

The use of a median filter in the manner described herein, in addition to allowing accurate detection to proceed even in the presence of noise such as GSM disturbance, also provides a means for making a simple detection as to whether an incoming signal is simply too noisy to be permitted to be detected. By comparing the processed signal (i.e., the signal after median filtering and post filtering, to the unprocessed signal, it is possible to define a "severe noise threshold" or "noise capture level" before the processed signal is supplied to the detector 8. If this threshold is exceeded, the signal is simply rejected outright, since it is assumed that the noise content of the signal is so high that, even though processed in accordance with the invention, making a detection based on that signal would be unacceptable suspect.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for removing an effect produced by an external disturbance on an internally obtained signal in an implantable cardiac stimulator, comprising the steps of:

intracorporeally acquiring an intracorporeally-produced physiological signal from a subject, said physiological signal representing data susceptible to a corrupting effect by an extracorporeally-produced disturbance resulting in a corrupted signal;

substantially removing said corrupting effect on said data in said corrupted signal while substantially preserving said data in said corrupted signal by median filtering said corrupted signal; and controlling intracorporeal administration of a medical therapy dependent on said data after median filtering said corrupted signal.

2. A method as claimed in claim 1 wherein the step of controlling intracorporeal administration of a medical therapy comprises:

detecting a selected characteristic from said data after median filtering of said corrupted signal;

producing a control signal dependent on said characteristic; and adjusting said medical therapy dependent on said characteristic.

3. A method as claimed in claim 1 wherein a step of intracorporeally acquiring an intracorporeally-produced physiological signal comprises intracorporeally acquiring a cardiac activity signal using an implanted electrode lead, said cardiac activity signal being susceptible to a corrupting effect by GSM disturbance.

4. A method as claimed in claim 3 wherein the step of controlling intracorporeal administration of a medical therapy dependent on said data comprises the steps of:

detecting a selected characteristic from said cardiac activity signal after median filtering said cardiac signal corrupted by said GSM disturbance;

generating a pacing control signal dependent on said characteristic; and using said pacing control signal to control a pulse generator, which emits stimulation pulses, to alter at least one of a stimulation rate and an amplitude of said stimulation pulses.

5. A method as claimed in claim 1 wherein said physiological signal is an analog signal, and comprising the additional step of converting said analog signal into a digital signal, and wherein the step of median filtering said corrupted signal comprises median filtering said corrupted signal in a digitally operating median filter.

6. A method as claimed in claim 1 wherein the step of median filtering said corrupted signal produces a median filtered signal, and comprising the additional step of post filtering said median filtered signal to produce a post filtered signal containing said data, and wherein the step of controlling intracorporeal administration of a medical therapy comprises controlling intracorporeal administration of a medical therapy dependent on the data contained in said post filtered signal.

7. A method as claimed in claim 6 wherein the step of post filtering said median filtered signal comprises bandpass filtering said median filtered signal.

8. A method as claimed in claim 6 comprising the additional steps of comparing said corrupted signal to said post filtered signal to identify a noise level in said corrupted signal, and preventing a post filtered signal, produced from a corrupted signal having a noise level which exceeds a predetermined threshold, from being used for controlling intracorporeal administration of said medical therapy.

9. A method as claimed in claim 1 wherein the step of median filtering said corrupted signal comprises median filtering said corrupted signal in a median filter having a three-point sorting network.

10. A method as claimed in claim 1 wherein the step of median filtering said corrupted signal comprises median filtering said corrupted signal in a median filter having a five-point sorting network.

11. An implantable cardiac stimulator comprising:

pulse generator means for emitting stimulation pulses having an amplitude and a rate;

a sensing amplifier;

an electrode lead, adapted for implantation in a subject, connected to said pulse generator means and to said sensing amplifier for delivering said stimulation pulses to cardiac tissue and for acquiring an electrical signal containing data representing cardiac activity, said electrical signal and the data contained therein being susceptible to a corrupting effect by an extracorporeally-produced disturbance resulting in a corrupted signal, said corrupted signal being supplied to said sense amplifier and said sense amplifier producing an amplifier output signal containing said data;

median filter means, supplied with said amplifier output signal, for substantially removing said corrupting effect on said data while substantially preserving said data by median filtering said amplifier output signal;

means, supplied with said data from said median filter means, for controlling intracorporeal administration of a medical therapy dependent on the data with said corrupting effect substantially removed therefrom after median filtering; and a housing adapted for implantation in a subject, said housing containing said pulse generator means, said sense amplifier, said median filter means and said means for controlling intracorporeal administration of a medical therapy.

12. A cardiac stimulator as claimed in claim 11 further comprising:

means for detecting a selected characteristic from said data after median filtering of said amplifier output signal;

means for producing a control signal dependent on said characteristic; and said means for controlling comprising means for adjusting said medical therapy dependent on said characteristic.

13. A cardiac stimulator as claimed in claim 12 wherein said means for adjusting said medical therapy comprises means for controlling said pulse generator means for adjusting at least one of said amplitude and said rate of said stimulation pulses.

14. A cardiac stimulator as claimed in claim 11 wherein said electrical signal acquired by said electrode lead is an analog signal, and said stimulator further comprising an analog-to-digital converter which converts said amplifier output signal into a digital signal, and wherein said median filter means comprises a digitally operating median filter supplied with said digital signal, said analog-to-digital converter being contained in said housing.

15. A cardiac stimulator as claimed in claim 11 wherein said median filter means produces a median filtered signal, and further comprising a post filter supplied with said median filtered signal which produces a post filtered signal containing said data, and wherein said means for controlling intracorporeal administration of a medical therapy comprises means for controlling intracorporeal administration of a medical therapy dependent on data contained in said post filtered signal, said post filter being contained in said housing.

16. A cardiac stimulator as claimed in claim 15 wherein said post filter comprises a bandpass filter.

17. A cardiac stimulator as claimed in claim 15 further comprising means for comparing said amplifier output signal to said post filtered signal for identifying a noise level in said amplifier output signal, and wherein said means for controlling comprises means for precluding use of a post filtered signal produced by an amplifier output signal containing a noise level which exceeds a predetermined threshold.

18. A cardiac stimulator as claimed in claim 11 wherein said median filter means comprises a three-point sorting network.

19. A cardiac stimulator as claimed in claim 11 wherein said median filter means comprises a five-point sorting network.

* * * * *